United States Patent
Nobis

(10) Patent No.: US 7,335,796 B2
(45) Date of Patent: Feb. 26, 2008

(54) PROCESS FOR THE PREPARATION OF KETONES BY OZONOLYSIS

(75) Inventor: Markus Nobis, Paderborn (DE)

(73) Assignee: Symrise GmbH & Co., KG, Holzminden (DE)

( * ) Notice: Subject to any disclaimer, the term of this patent is extended or adjusted under 35 U.S.C. 154(b) by 113 days.

(21) Appl. No.: 11/396,902

(22) Filed: Apr. 4, 2006

(65) Prior Publication Data

US 2006/0224019 A1  Oct. 5, 2006

(30) Foreign Application Priority Data

Apr. 5, 2005  (DE)  ............ 10 2005 015 590

(51) Int. Cl.
*C07C 45/40* (2006.01)

(52) U.S. Cl. .................................. 568/357; 568/403

(58) Field of Classification Search .............. None
See application file for complete search history.

(56) References Cited

FOREIGN PATENT DOCUMENTS

| EP | 0 822 191 | 2/1998 |
|----|-----------|--------|
| EP | 1 215 190 | 6/2002 |

*Primary Examiner*—Sikarl A. Witherspoon
(74) *Attorney, Agent, or Firm*—Roylance, Abrams, Berdo & Goodman, L.L.P.

(57) ABSTRACT

The invention relates to a process for the preparation of a ketone from a tertiary alcohol having a double bond in the alpha position, that includes the step of contacting tertiary alcohol having a double bond in the alpha position with ozone in the presence of an inorganic base under ketone-forming reaction conditions.

8 Claims, No Drawings

PROCESS FOR THE PREPARATION OF KETONES BY OZONOLYSIS

FIELD OF THE INVENTION

The invention relates to a process for the preparation of a ketone from an alcohol having a double bond in the alpha position.

BACKGROUND

Alcohols having a double bond in the alpha position are conventionally converted into ketones in the presence of inorganic oxidizing agents (e.g. $KMnO_4$, $OsO_4$, $H_2SO_4$/ $H_2CrO_4$). In particular, it is known to convert an alcohol of the formula (I) into a ketone of the formula (II) in this manner:

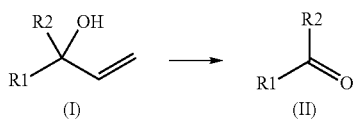

wherein the radicals R1, R2 independently of one another can be alkyl, alkenyl, cycloalkyl or aryl. Alcohols of the formula (I) are obtained from natural sources in some cases, but are also accessible by synthesis.

WO 91/09852 describes a two-stage process for the preparation of sclareolide (also (−)-norlabdan oxide) from sclareol, in which in a first stage an oxidative degradation of sclareol in the presence of ruthenium salts or potassium permanganate takes place, and in a second stage the intermediate product formed is oxidized with peracid and/or peracid salts to give sclareolide.

Barton et al. (Tetrahedron Letters, 1994, 35(32), 5801) describe a further synthesis set-up for the preparation of sclareolide starting from sclareol, and in particular by oxidative reaction of the starting substance with a mixture of $OsO_4/NaIO_4$.

The oxidizing agents used in conventional processes are a disadvantage because of their toxicity to man and the environment and their ease of handling being made difficult as a result. This disadvantage in particular makes the industrial reaction of alcohols having a double bond in the alpha position difficult.

Attempts have therefore been made to modify these processes, and in particular to use novel oxidizing agents. Thus, EP 0 822 191 A1 and Fekih et al. (J. Soc. Chim. Tunisie, 2001, 4(9), 909) each describe two-stage processes for the preparation of sclareol oxide from sclareol by ozonolysis:

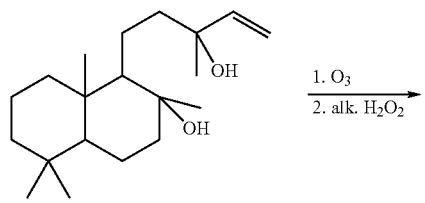

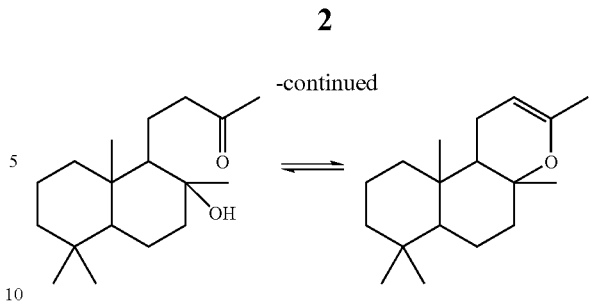

In a first stage, the allyl alcohol group of the sclareol is converted into the corresponding ozonide by addition of ozone. In a second stage, the ozonide is then converted into the desired sclareol oxide by working up with alkaline $H_2O_2$. The reaction can be carried out in various organic solvents, such as methylene chloride, methanol or ethanol. In the reaction, however, large amounts of the highly reactive ozonide are obtained in the first step, so that considerably safety precautions are necessary for carrying out the reaction. In particular, an efficient cooling is required in order to be able to carry out the reaction safely. These disadvantages are important in particular in an industrial reaction.

DETAILED DESCRIPTION

The invention is based on the object of providing a process for the preparation of a ketone from a tertiary alcohol having a double bond in the alpha position which limits or completely avoids the abovementioned disadvantages of conventional processes. In particular, it should be possible to carry out the process without the high safety precautions hitherto necessary.

The object is achieved by a process for the preparation of a ketone from a tertiary alcohol having a double bond in the alpha position, comprising the step including contacting tertiary alcohol having a double bond in the alpha position with ozone in the presence of an inorganic base under ketone-forming reaction conditions.

The process according to the invention leads to a surprisingly short reaction time with a simultaneously high yield, and avoids the occasional occurrence of large amounts of heat. Furthermore, the use of highly toxic oxidizing agents is dispensed with, so that overall lesser safety precautions have to be taken than with conventional processes.

The possibility of achieving high yields with a simultaneously short reaction time was surprising in particular since it was known that in the presence of an inorganic base, ozone dissociates rapidly, especially at weakly basic pH values (Hollemann, Wiberg, Lehrbuch der Anorganischen Chemie [Textbook of Inorganic Chemistry], 101st ed., p. 516). Accordingly, it was to be expected that large amounts of ozone would be required in order to provide a sufficient amount of ozone for reaction of the alcohol. It has now been found, surprisingly, that the amount of ozone required is not increased compared with conventional processes, in spite of the presence of an inorganic base, and that the reaction according to the invention, which is carried out in one step, can even be carried out significantly more rapidly and with a lower requirement of safety precautions than in the case of conventional processes.

A further advantage of the process according to the invention is that only small amounts of heat are released. Compared with conventional processes, only cooling units having a lower output are therefore required for carrying out the process according to the invention. This is a great advantage in particular in an industrial process procedure.

Particularly good results can be obtained if the alcohol employed is treated with 1-3 molar equivalents of ozone, based on the alcohol group to be reacted. In this context, a process according to the invention in which the alcohol employed is treated with 1-2 molar equivalents of ozone, based on the alcohol group to be reacted, is particularly preferred. In both cases, the amount of ozone employed is advantageously kept low. This is of advantage in particular in an industrial process procedure, since ozone is expediently generated in a reaction which runs in parallel during the reaction of the alcohol and is added constantly or continuously to the reaction. The process according to the invention therefore renders possible a reaction of the alcohol with a low requirement of ozone to be provided.

For generation of the ozone in an ozone generator, pure oxygen, but also mixtures of oxygen and inert gases in various volume ratios to oxygen, preferably between 1 and 80 vol. %, can be used. An ozone content of a gas passed into the reaction mixture in step b) is preferably in the range of from 1 to 12 wt. %, based on the gas employed, but particularly preferably in the range of from 4 to 8 wt. %. The ozone can be passed into the reaction mixture in a molar amount in the range of from 1 to 5, preferably in the range of from 1 to 3, particularly preferably in the range of from 1.1 to 2 molar equivalents to the double bond to be reacted in the alpha position of the compound. By-products of the ozonolysis can be decreased by this means.

It is furthermore preferable if the base is not already initially introduced completely at the start of the reaction, but is added constantly such that its equivalent concentration on discontinuation of the reaction is 1 to 3, preferably 1 to 2, based on the total alcohol groups to be reacted which are employed. It is ensured in this way that the concentration of available ozone is at the optimum level to achieve a rapid reaction of the alcohol with high yields, and at the same time is low enough to prevent the release of high amounts of heat. The base can be added continuously or repeatedly.

Suitable inorganic bases are all the strong to medium-strong Brönstedt bases which are stable under ozonolysis conditions. The pKB value of the base is preferably 4 to 10. The base used is preferably chosen from the group consisting of NaOH, KOH, LiOH, $NaHCO_3$, $Na_2CO_3$, $CaCO_3$ or mixtures of two or more of these bases. In this context, the alkali metal bases mentioned are in turn advantageous, and the alkali metal hydroxides are preferred. LiOH, NaOH and KOH are particularly preferred bases. In the process according to the invention, with alkali metal bases, no corresponding alkali metal peroxides or alkali metal ozonides are formed or accumulated, in contrast to the process described in U.S. Pat. No. 3,664,810 with alkaline earth metal bases, in which substantially stoichiometric amounts of the corresponding alkaline earth peroxides are formed. These bases, in particular the alkali metal hydroxides (which are mentioned as particularly preferred) have given particularly high yields of the desired compound in comparison experiments. The bases are expediently provided in dissolved form in step b), so that when choosing the base, the solubility thereof in the solvent used is also to be taken into account.

EP 1 569 885 relates to the in situ dissociation of peroxides during the ozonolysis of optionally substituted alkenes to give the corresponding aldehydes or ketones. $CaCO_3$, inter alia, can be used as the support material for the peroxide-dissociating metal catalysts used there. According to EP 1 569 885, $CaCO_3$ is not employed for its basic properties, but, on the contrary, as an inert carrier material which does not dissolve in the solvent (mixture) employed in the ozonolysis and therefore also makes no noticeable contribution to the pH.

The process according to the invention is preferably carried out a pH in the range of from 13 to 8. The pH is regularly initially in the range of from 13 to 12 during the ozonolysis in the presence of the base of the process according to the invention, and in the range of from 9 to 8 at the end of the ozonolysis. In this context, it is to be noted that the selectivity of the ozonolysis in the process according to the invention substantially does not decrease as the duration of the reaction progresses. This is all the more surprising, since it is known that the stability of ozone decreases noticeably at lower pH values (below 14) (Hollemann, Wiberg, Lehrbuch der Anorganischen Chemie [Textbook of Inorganic Chemistry, 101st ed., p. 508, 517). It would have been expected that the dissociation products of ozone would have reacted with the tertiary alcohols having a double bond in the alpha position which are to be employed according to the invention, to give undesirable by-products or degradation products of the tertiary alcohols.

In preferred embodiments, the process according to the invention is carried out in the absence of a heterogeneous, inorganic peroxide-dissociating catalyst from the group consisting of iridium, manganese, cobalt, silver, gold, palladium, platinum or ruthenium.

In further preferred embodiments, the process according to the invention is carried out in the absence of an emulsifier.

Water or a solvent mixture of water and a water-miscible organic solvent is preferably employed as the solvent for the base. The solvent mixture preferably comprises tetrahydrofuran and water, in particular with a mixture ratio by weight of tetrahydrofuran to water in the range of from 1:2 to 2:1, particularly preferably about 1:1. The solvent must be suitable for the ozonolysis. The base is preferably added in step b) by dropwise addition from a stock solution, the concentration of the base in the stock solution preferably being 2 to 50 wt. %, particularly preferably 7.5 to 10 wt. %, in each case based on the total stock solution.

The solvent for the alcohol is chosen such that it is completely or largely inert towards ozone and is completely or largely stable towards the base added. Preferred solvents for the alcohol include substituted or unsubstituted aromatic hydrocarbons, or solvents which contain oxygen in the form of carbonyl, ether or alcohol functionalities. Halogenated aromatic and non-aromatic solvents likewise prove to be suitable for carrying out the reaction. Solvents with other oxidizable heteroatoms (nitrogen and sulfur) are not suitable because of their affinity for oxygen. Toluene is particularly preferred.

It is particularly preferable for the reaction to be carried out in a two-phase system, the alcohol being provided in an organic solvent and the base being employed in an aqueous solvent. This has the advantage that precipitation of the base on addition into the reaction mixture is prevented, a concentration of the base in the phase of the reaction mixture containing the alcohol remains low, and a reaction between the ozonide formed and the base takes place only in the region of the phase boundary. In this context, the reaction mixture is expediently mixed thoroughly by stirring. Particularly preferably, the solvent of the alcohol is toluene and the solvent of the base is water or a solvent mixture of water and tetrahydrofuran, in particular with a mixture ratio by weight of tetrahydrofuran to water in the range of from 1:2 to 2:1, particularly preferably about 1:1.

Preferably, the base is added to the reaction mixture with a rate of addition which depends on the amount of ozonide formed. As a rule, the rate of addition of the base is increased when the amount of ozonide formed also increases during the period in question, and vice versa. It is particularly preferable for the dissolved base to be added in a molar amount of between 0.8 to 1.2 molar equivalents to the ozonide formed. By this means, the concentration of the ozonide in the reaction mixture can be kept low, but possible side reactions or disturbances in the formation of the ozonide due to the base added are avoided.

Preferably, the reaction temperature is −78° C. to +30° C., in particular −30° C. to +10° C., particularly preferably −10° C. to 0° C. By this means, side reactions of the ozonolysis and during the further reaction of the ozonide formed and the base can be suppressed, but at the same time sufficiently high conversions for the two component reactions can still be maintained.

The alcohol employed in a process according to the invention, in particular by one of the preferred process embodiments described above, preferably has the general formula (Ia)

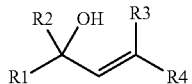

(Ia)

wherein R1 and R2 independently of one another denote an organic radical and the two radicals R1 and R2 together can form a ring, and wherein furthermore R3 and R4 independently of one another can denote hydrogen or substituted or unsubstituted alkyl, alkenyl, cycloalkyl or aryl and the two radicals together can form a ring and/or one or both of the radicals R3 and R4 can form a ring together with one or both of the radicals R1 and/or R2.

The process according to the invention can thus be carried out with an advantageously wide choice of tertiary alcohols.

In preferred alcohols, R1 and R2 independently of one another are chosen from organic radicals having up to 30 carbon atoms and up to 10 nitrogen and/or oxygen atoms.

Preferably, R1 and R2 independently of one another denote substituted or unsubstituted alkyl, alkenyl, cycloalkyl, cycloalkylalkyl, heterocycloalkyl or (hetero)aryl, wherein R1 and R2 together can form a ring, preferably a ring having 5 to 20 members in total.

Particularly preferably, R1 and R2 independently of one another denote substituted or unsubstituted alkyl, alkenyl, cycloalkyl, cycloalkylalkyl or aryl.

Preferably, R3 and R4 independently of one another denote hydrogen or substituted or unsubstituted alkyl, alkenyl, cycloalkyl, cycloalkylalkyl, heterocycloalkyl or (hetero)aryl, wherein R3 and R4 together can form a ring, preferably a ring having 5 to 20 members in total.

If R1, R2, R3 and/or R4 are cyclic radicals, these are also to be understood as meaning rings bonded to one another, such as e.g. fused, polycyclic or condensed rings.

R1 and R2 furthermore independently of one another preferably denote substituted or unsubstituted straight- or branched-chain $C_1$-$C_{20}$-alkyl, straight- or branched-chain $C_3$-$C_{20}$-alkenyl, $C_3$-$C_{20}$-cycloalkyl, $C_4$-$C_{20}$-cycloalkylalkyl, $C_3$-$C_{20}$-heterocycloalkyl or $C_5$-$C_{20}$-(hetero)aryl.

R3 and R4 furthermore independently of one another preferably denote hydrogen or substituted or unsubstituted straight- or branched-chain $C_1$-$C_{20}$-alkyl, straight- or branched-chain $C_3$-$C_{20}$-alkenyl, $C_3$-$C_{20}$-cycloalkyl, $C_4$-$C_{20}$-cycloalkylalkyl, $C_3$-$C_{20}$-heterocycloalkyl or $C_5$-$C_{20}$-(hetero)aryl.

If R1, R2, R3 and/or R4 are substituted alkyl, alkenyl, cycloalkyl, cycloalkylalkyl, heterocycloalkyl or (hetero)aryl, in each case the following substituents are preferred:

hydroxyl, $C_1$-$C_8$-alkyl, preferably methyl, ethyl, n-propyl, iso-propyl, n-butyl, iso-butyl, tert-butyl, $C_3$-$C_{18}$-cycloalkyl, preferably cyclopropyl, cyclopentyl, cyclohexyl, cyclooctyl, cyclododecyl, cyclopentadecyl, cyclohexadecyl, $C_2$-$C_8$-alkynyl, preferably ethynyl, propynyl $C_1$-$C_8$-perfluoroalkyl, preferably trifluoromethyl, $C_1$-$C_4$-alkoxy, preferably methoxy, ethoxy, iso-propoxy, n-butoxy, iso-butoxy, tert-butoxy, $C_3$-$C_{12}$-cycloalkoxy, preferably $C_3$-cycloalkoxy, $C_5$-cycloalkoxy, $C_6$-cycloalkoxy, $C_8$-cycloalkoxy, $C_{12}$-cycloalkoxy, $C_{15}$-cycloalkoxy, $C_{16}$-cycloalkoxy, $C_1$-$C_{20}$-alkoxyalkyl, in which 1 to 5 $CH_2$ groups are replaced by oxygen, preferably —[—O—$CH_2$—$CH_2$—]$_n$-Q or —[—O—$CH_2$—CHMe-]$_n$-Q, wherein Q is OH or $CH_3$ and wherein n can denote 1 to 4, $C_1$-$C_4$-acyl, preferably acetyl, $C_1$-$C_4$-carboxy, preferably $CO_2Me$, $CO_2Et$, $CO_2i$-Pr, $CO_2^tBu$, $C_1$-$C_4$-acyloxy, preferably acetyloxy, halide, preferably F or Cl, and $Si_1$-$Si_{30}$-siloxy.

Good results are obtained in particular if the double bond in the alpha position is not part of a system of conjugated double bonds. Preferably, the radicals R3 and R4 are therefore hydrogen or alkyl. In this context, alcohols in which R3 and R4 are hydrogen are particularly preferred.

If the alcohol to be reacted carries further alcohol groups or other groups which are not be reacted, in addition to an alcohol group which is to be reacted, these alcohol groups are expediently protected against ozonolysis.

The process is suitable in particular for compound chosen from the group consisting of manool, sclareol, larixol, linalool, nerolidol or a derivative derived from the compounds mentioned. Derivatization of the compounds serves in particular to introduce protective groups for non-allylic double bonds (double bonds which are not in the alpha position) optionally present, preferably by selective epoxidation thereof.

The invention is explained in more detail in the following with the aid of embodiment examples.

EXAMPLES

The reactions were carried out in conventional laboratory apparatuses. In smaller batches, the reaction mixtures were kept at the appropriate temperature by dry ice baths. In the case of larger batches, double-jacketed vessels through which a cooling medium suitable for the desired temperature range was pumped were used.

Non-allylic double bonds present in the compounds were as a rule protected from ozonolysis by epoxidation.

Unless stated otherwise, all data in % are to be understood as % by weight data. Amounts data in the examples relate to weight ratios.

The following compounds having a diterpene base structure were employed as educts in Examples 1 to 5:

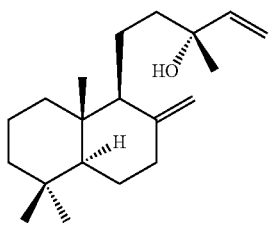

Manool (III)

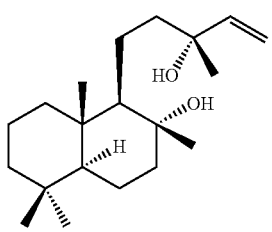

Sclareol (IV)

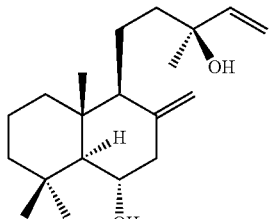

Larixol (V)

The compounds manool (III), sclareol (IV) and larixol (V) are accessible from plant raw materials by extraction and are distinguished by a tertiary alcohol function with an allylic substituent.

Example 1

Reaction of Manool (III)

a) Epoxidation

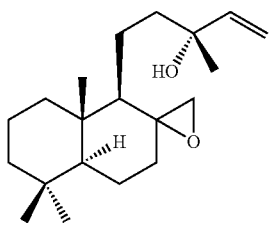

(IIIa)

45 g/0.16 mol manool (III) was initially introduced into 150 g toluene, and 0.32 g tetrabutylammonium hydrogen sulfate was added. After addition of 150 g water, 110 g/0.22 mol magnesium monoperoxyphthalate were added. After 4 h at 40° C., the organic phase was separated off. The organic phase separated off was washed free from peroxide with sodium sulfite solution, after neutralization by saturated $Na_2CO_3$ solution. 39.8 g of a product comprising the compound (IIIa) in 80% purity (GC-MS) were obtained. The product was employed in the ozonolysis without further working up.

b) Ozonolysis

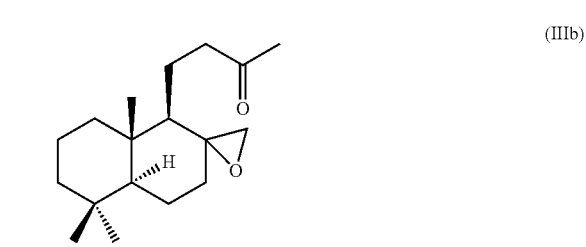

(IIIb)

28.3 g/0.08 mol of compound (IIIa) were dissolved in nine times the amount of toluene and the solution was cooled to −25° C. 2 molar equivalents of ozone were passed at a constant rate into the reaction mixture, while stirring and cooling. 1.1 molar equivalents of 5% strength aqueous NaOH solution were simultaneously added dropwise to the reaction mixture over the entire duration of the passing in of the ozone, a rate of addition of the solution being kept constant. A conversion of the compound (IIIa) was monitored by means of GC. After complete conversion, the reaction mixture was warmed to room temperature, the aqueous phase was separated off and the organic phase was washed neutral with aqueous saturated NaCl solution.

Yield of compound (IIIb): 21.6 g (71%)

Example 2

Reaction of Larixol (V)

a) Epoxidation

(Va)

15 g/0.06 mol larixol (V) were initially introduced into 150 g toluene. After addition of 150 g water, 27.4 g magnesium monoperoxyphthalate were added. After stirring for 4 h at 40° C., the organic phase was separated off. After neutralization with aqueous saturated NaCl solution, this was washed free from peroxide using sodium sulfite solution. 16.5 g of a product comprising the compound (Va) in 91% purity (GC-MS) were obtained. The product was employed in the ozonolysis without further working up.

b) Ozonolysis

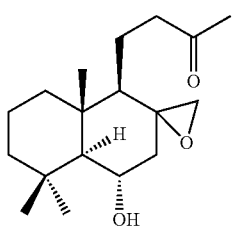

(Vb)

20.0 g/0.06 mol of compound (Va) were dissolved in 200 g CH$_2$Cl$_2$, while stirring, and the solution was cooled to −40° C. 2.5 molar equivalents of ozone were passed at a constant rate into the cooled solution, while stirring and cooling. A solution of 1.2 molar equivalents of NaOH (2.9 g/0.07 mol), dissolved in 52 g tetrahydrofuran and 52 g water, was added dropwise at a constant rate over the entire duration of the passing in of ozone. After the excess ozone had been driven off, the reaction batch was warmed to room temperature and then neutralized with aqueous saturated NaCl solution and freed from the peroxides formed by washing with sodium sulfite solution. The crude product (Vb) was obtained as a pale to colourless oil after the solvent had been distilled off.

The yield is 70% (GC-MS), calculated for compound (V).

Example 3

Ozonolysis of Sclareol (IV)

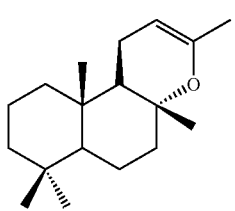

(IVa)

30.8 g/0.1 mol sclareol (IV) were dissolved in 4.5 times the amount of methanol/CH$_2$Cl$_2$ (1:1 (w/w)) and the reaction mixture was cooled to −20° C. 2 molar equivalents of ozone were then passed at a constant rate into the reaction mixture, while stirring and cooling. During the addition of the ozone, 1.1 molar equivalents of NaOH, based on the sclareol and dissolved in five times the amount of water and tetrahydrofuran, were added dropwise into the reaction mixture at a constant rate. When the reaction had ended, the reaction mixture was warmed to room temperature and the organic phase was separated off. After neutralization with aqueous saturated NaCl solution and destruction of the peroxides formed with sodium sulfite solution, the solvent was distilled off and the reaction product sclareol oxide (IVa) was obtained with a yield of 97% (GC-MS).

Example 4

Ozonolysis of Sclareol (IV) Using Various Bases 162 g/0.5 mol sclareol (IV) were dissolved in nine times the amount of toluene and the reaction mixture was cooled to −5° C. 2 molar equivalents of ozone were then passed at a constant rate into the reaction mixture, while stirring and cooling. During the addition of the ozone, 1.5 molar equivalents of the bases mentioned in Tab. 1, based on the sclareol (IV) and dissolved in five times the amount of water and tetrahydrofuran, were added dropwise into the reaction mixture at a constant rate. When the reaction had ended, the reaction mixture was warmed to room temperature and the organic phase was separated off. After neutralization of the organic phase with aqueous saturated NaCl solution, washing with a sodium sulfite solution and distilling off of the solvent, the reaction product was obtained as a yellow solid and the content of sclareol (IV) and sclareol oxide (IVa) was determined by GC-MS (see Table 1).

The highest selectivity in the conversion of sclareol (IV) into sclareol oxide (IVa) was achieved with a solution of KOH.

TABLE 1

| Base | Conversion$_{sclareol}$ [%] | Sclareol (IV) [%] | Sclareol oxide (IVa) [%] |
|---|---|---|---|
| KOH | 99.5 | 0.5 | 96.4 |
| NaHCO$_3$ | 96.5 | 3.5 | 79.4 |
| Na$_2$CO$_3$ | 99.5 | 0.5 | 62.9 |
| CaCO$_3$ | 98.1 | 1.9 | 78.0 |

Example 5

Ozonolysis of Manool (III)

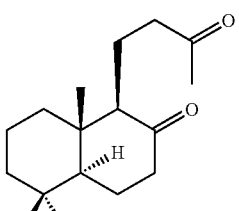

(IIIc)

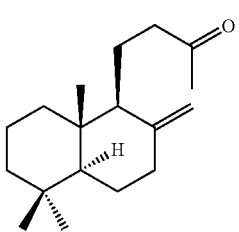

(IIId)

82.0 g/0.20 mol manool (III) (70% pure natural substance) were initially introduced into 250 g toluene and the solution was cooled to −5° C. 2.5 molar equivalents of ozone were then passed at a constant rate into the reaction mixture, while stirring and cooling. A solution of 12 g/0.3 mol NaOH and water (weight ratio 1:9) was added dropwise to the reaction mixture at a constant rate during the entire reaction time. When the passing in of the ozone had ended, the reaction mixture was warmed to room temperature and the organic phase was separated off. The organic phase was neutralized by washing several times with water. After concentration of the organic phase, the crude product was obtained as a colourless oil.

Composition (GC-MS): Compound (IIIc) 66%
Compound (IIId) 33%

Example 6

Reaction of Linalool (VI)

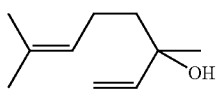
(VI)

a) Epoxidation

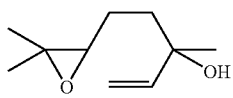
(VIa)

7.7 g linalool (VI) were dissolved in 100 g toluene, 0.1 g tetrabutylammonium hydrogen sulfate was added and the reaction and working up were carried out analogously to the instructions under Example 1, a) Epoxidation.

Crude yield: 7.4 g, content in this of compound (VIa) 88% b) Ozonolysis

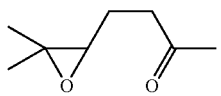
(VIb)

5.0 g of compound (VIa) were dissolved in 100 g $CH_2Cl_2$ and reacted analogously to the instructions under Example 1, b) Ozonolysis. After working up of the reaction mixture (washing neutral with NaCl solution, washing with sodium sulfite), 2.15 g 5,6-epoxy-6-methyl-heptan-2-one (VIb) were obtained (yield: 49% (GC-MS)).

Example 7

Reaction of Nerolidol (VII)

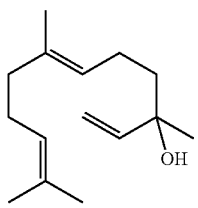
(VII)

a) Epoxidation

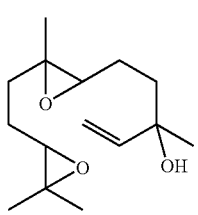
(VIIa)

22.0 g nerolidol (VII) were dissolved in 100 g toluene, 0.3 g tetrabutylammonium hydrogen sulfate was added and the reaction and working up were carried out analogously to the instructions under Example 1, a) Epoxidation.

13.9 g of compound (VIIa) were obtained.

b) Ozonolysis

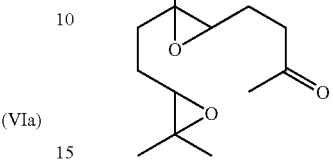
(VIIb)

7.5 g of compound (VIIa), dissolved in 100 g $CH_2Cl_2$, were initially introduced into the reaction vessel. 2.5 molar equivalents of ozone were then passed at a constant rate into the reaction mixture at −40° C., while stirring. 1.1 molar equivalents of NaOH, dissolved in nine times the amount of water/tetrahydrofuran (1/1, w/w) were passed in at a constant rate during the entire reaction. When the ozonolysis had ended, the reaction mixture was warmed to room temperature and the organic phase was separated off. After neutralization of the organic phase with water and removal of the solvent by distillation, compound (VIIb) was obtained as a colourless oil.

Yield: 4.33 g (43.70%)

The invention claimed is:

1. Process for the preparation of a ketone from a tertiary alcohol having a double bond in the alpha position, comprising the step: contacting tertiary alcohol having a double bond in the alpha position with ozone in the presence of an inorganic base under ketone-forming reaction conditions.

2. Process according to claim 1, characterized in that the alcohol is contacted with 1-3 molar equivalents of ozone per alcohol group to be treated.

3. Process according to claim 1, wherein the base is added such that its equivalent concentration is 1 to 3 based on the alcohol group to be treated.

4. Process according to claim 1 wherein said base is chosen from the group consisting of NaOH, KOH, LiOH, $NaHCO_3$, $Na_2CO_3$, $CaCO_3$ or mixtures of two or more of these bases.

5. Process according to claim 1 wherein said alcohol is in an organic solvent and said base is employed in an aqueous solvent.

6. Process according to claim 1 wherein said reaction conditions comprise a reaction temperature in the range of from −78° C. to +30° C.

7. Process according to claim 1 wherein said alcohol has the general formula (Ia):

(Ia)

wherein:
R1 and R2 independently of one another denote an organic radical and the two radicals R1 and R2 together can form a ring,
R3 and R4 independently of one another can denote hydrogen or substituted or unsubstituted alkyl, alkenyl, cycloalkyl or aryl and the two radicals together can form a ring and/or one or both of the radicals R3 and R4 can form a ring together with one or both of the radicals R1 and/or R2.

8. Process according to claim 1 wherein said alcohol is chosen from the group consisting of

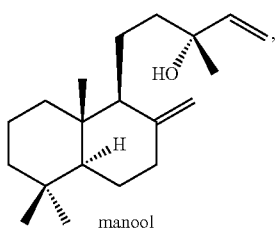

manool (III)

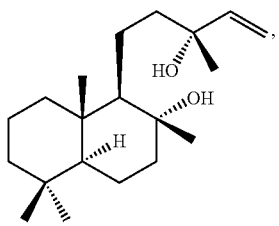

sclareol (IV)

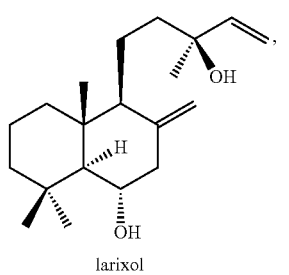

larixol (V)

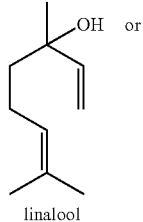

linalool (VI) or

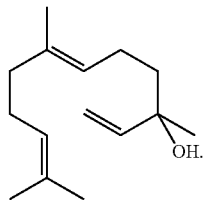

nerolidol (VII)

* * * * *